United States Patent [19]

Chamberland et al.

[11] 4,388,155
[45] Jun. 14, 1983

[54] SOLID SENSOR FOR ANHYDRIDES

[75] Inventors: André M. Chamberland, Mont St-Hilaire; Michel Gauthier, Laprairie, both of Canada

[73] Assignee: Hydro-Quebec, Montreal, Canada

[21] Appl. No.: 174,186

[22] Filed: Jul. 31, 1980

Related U.S. Application Data

[60] Division of Ser. No. 718,511, Aug. 30, 1976, Pat. No. 4,282,078, and a continuation-in-part of Ser. No. 472,904, May 23, 1974, abandoned.

[51] Int. Cl.³ .............................................. G01N 27/46
[52] U.S. Cl. .................................. 204/1 T; 204/410; 204/426; 204/427
[58] Field of Search ............................. 204/1 S, 195 S

[56] References Cited

U.S. PATENT DOCUMENTS

| | | | |
|---|---|---|---|
| 3,400,054 | 9/1968 | Ruka et al. | 204/195 S |
| 3,506,492 | 4/1970 | Buzzelli et al. | 429/191 |
| 3,620,931 | 11/1971 | Reichner | 204/195 S |
| 3,718,546 | 2/1973 | Salzano et al. | 204/195 R |

FOREIGN PATENT DOCUMENTS

| | | |
|---|---|---|
| 1954663 | 5/1970 | Fed. Rep. of Germany . |
| 2349062 | 4/1974 | Fed. Rep. of Germany . |
| 21673 | 8/1961 | German Democratic Rep. . |
| 61367 | 4/1968 | German Democratic Rep. . |

*Primary Examiner*—T. Tung
*Attorney, Agent, or Firm*—Schwartz, Jeffery, Schwaab, Mack, Blumenthal & Koch

[57] ABSTRACT

The invention concerns a detector for anhydrides, present in the air or stack gases, which comprises a solid state electrolyte element containing oxy-anions of the particular anhydride to be detected. This solid state element is provided with metal areas to which potentiometric measuring means are connected. The detecting element is, preferably, sintered and may consist of one or several juxtaposed solid state compounds, according as the reference source is a gas or a solid state electrode, respectively. The electrolyte element is heated to a temperature not exceeding its fusion point. In addition, particular arrangements are provided to compensate for the oxygen content variations in air due to varying measurement conditions.

2 Claims, 12 Drawing Figures

SOLID SENSOR FOR ANHYDRIDES

This is a continuation-in-part of application Ser. No. 472,904, filed on May 23, 1974, now abandoned, and a division of application Ser. No. 718,511, filed Aug. 30, 1976 now U.S. Pat. No. 4,282,078.

The present invention relates to a sensing device for detecting and measuring the activity of a gas by means of a solid state sensing element. In particular, the invention concerns electrochemical means useful in detecting an anhydride or gases containing anhydrides or related compounds in air or in oxygen bearing gas.

The invention is remarkable in that it permits a quantitative determination of the activity of anhydrides and related compounds which pollute surrounding air, such detection being realized by means of a solid state sensor supplying an oxy-anion of the corresponding anhydride.

Hitherto, research directed to the atmospheric pollution measurement has been oriented so as to replace so-called first generation monitors which mainly use liquid scrubbers to sample the air.

Among the atmospheric pollutants, sulfur bearing compounds and nitrogen oxydes are considered as the most harmful agents to people and among the most agressive to materials. Because of the wide concentration range that usually exists between industrial stack gases and ambient air, it is rather difficult to build a sensor able to directly monitor the ambient air and other polluting sources of high concentration. A $SO_2$ activity measuring device based on a concentration cell principle is described in U.S. Pat. No. 3,718,546 issued on Feb. 27 1973 to Salzano et al. This device uses fused salts as electrolytes, thus cumbersome and rather difficult to transport. In addition, a great stability is required in the flow of gases to obtain realistic measurements.

A prime purpose of the present invention consists in providing an improved means for the detection of anhydrides or related compounds mixed with an oxygenated gas.

In particular, the present invention is useful for quantitavely determining extremely small and high concentrations of sulfur bearing compounds in gas phases by means of an element containing oxy-anions of the anhydride to be detected.

Another object of the invention is to provide a solid state detecting device the operation of which is independent of the flow of the gas used as a reference source or of the gas the concentration of which is to be measured.

A further object of the present invention resides in providing various types of solid state electrodes as reference sources thereby eliminating the inconveniences inherent to the use of gas as the reference sources, which substantially increases the miniaturization of the sensing device of the invention and thus decreases its cumbersomeness.

An additional object of the invention consists in providing a detecting device which may be mounted in a relatively small, compact and portable apparatus readily usable on a site where particular gases or vapors bearing anhydrides or related compounds have to be analyzed.

Another object of the invention is to provide a detector for anhydrides which is easy to build, has a relatively long useful life and a good calibration stability.

A further object of the invention consists in providing a detecting device able to detect without interference anhydride bearing compounds mixed with other vapors or gases.

A further object of the invention resides in an improved detector wherein the electro-motive force or potential difference detected signal represents the logarithm of the concentration of the anhydride and is substantially linear.

An additional object of the invention consists in providing appropriate means to compensate oxygen partial pressure variations in particular gases like stack gases.

Another object of the invention is to provide particular arrangements of inlet and outlet conduits leading the gas in contact with the detecting element in order to minimize any dead volume of gas therein and to optimize the response time of the detector. These preferred arrangements greatly enhance miniaturisation of the detector and its operating modes.

The above-mentioned objects of the present invention are actually achieved through a sensor which comprises a solid state electrolyte element containing oxy-anions of the anhydride to be detected, this solid state element being provided with electrodes to which potentiometric measuring means are connected. This detecting element is made up of one or more juxtaposed chemical compounds. Moreover, heating means are provided to increase the sensing capacity of the electrolytic element, the heating of the latter being however at a temperature such that a logarithmic variation of the activity of the anhydride to be detected will result in a proportional and substantially linear variation of the difference of potential detected at the electrodes. In any case, the heating temperature will be below the fusion temperature of the electrolyte elements.

The above and other objects will become apparent through the following description of preferred embodiments given with reference to the accompanying drawings, wherein FIG. 1 schematically illustrates an embodiment of the present invention wherein a solid state electrolyte element is flanked with porous detection and reference electrodes, a standard anhydride-containing gas being used as a reference;

FIG. 9 schematically illustrates three preferred arrangements of the anhydride detectors. Gas circulation chambers are formed by a system of small diameter parallel holes, inside a quartz or alumina rod. One end of this rod is mechanically pressed against the solid electrolyte in such a way as to seal the gas chambers by thermal deformation of the solid electrolyte. A gas circulating path is achieved between the inlet and the outlet chambers by perforating the common wall of these chambers in the vicinity of the solid electrolyte electrode.

Figure 1:
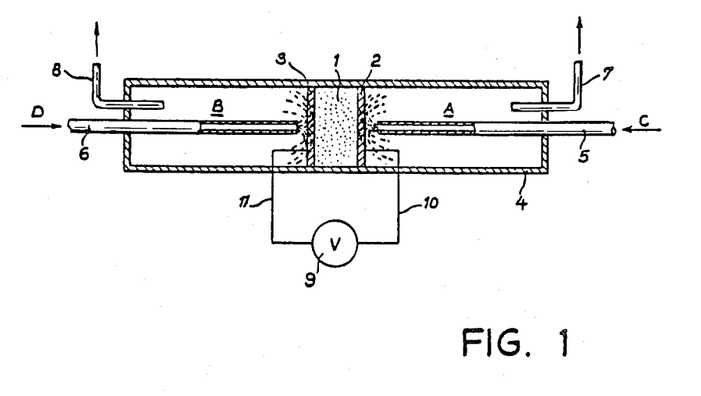

FIG. 1 illustrates a first sensor. This sensor comprises a detecting element 1 constituted of an electrolyte containing oxy-anions of the gaseous anhydride to be analyzed. The element 1 is made up of an alkali metal salt or an alkaline earth metal salt.

That element 1 is preferably pellet shaped, but, of course, any other form is also quite acceptable. Each end of the element 1 is in contact with an electronically conductive porous material 2 and 3 such as silver, platinum, gold or other.

The electrolyte element 1 is tightly inserted into a tube 4 made of alumina so as to hermetically separate a measure compartment "A" from a reference compartment "B". Each end of the tube 4 is sealed with any appropriate material.

A sample "C" of the anhydride the concentration of which is to be determined is introduced into the measure compartment "A" through a conduit 5. Similarly, a corresponding anhydride "D" of known concentration is introduced into the reference compartment "B" via a conduit 6. These gas supply conduits 5 and 6 are suitably disposed axially and at the center of the alumina tube 4 so as to provide a better contact for each of the gases with the corresponding metal surface and the electrolyte. The anhydride gases are thereafter exhausted through outlet tubes 7 and 8 respectively extending from each of the compartments to the outside.

It is to be noted that the metal surfaces or electrodes 2 and 3 are at such a porosity as to permit and to carry out the triple contact between the electrolyte element 1, the gas "C" or "D" and the respective electrodes 2 and 3. In practice, however, those metal electrodes 2 and 3 need not entirely cover the corresponding electrolyte element surfaces, but are rather made up of metal dots deposited thereon. In the latter case, the metal electrodes present a non-porous structure.

Each of the metal surfaces 2 and 3 are connected to the terminals of a potentiometric measuring instrument 9, such as a voltmeter, by means of conductive wires 10 and 11. The measuring instrument 9 operates to indicate the difference of potential existing between the electromotive forces built-up on each of the conductive surfaces 2 and 3 when in contact with the sampled gas, and the reference gas, respectively.

In order to increase the sensing capacity of the element 1, by increasing its ionic conductivity, thereby allowing occurrence of rapid electrochemical reactions at the electrodes between the gaseous anhydrides and the oxy-anions of the electrolyte, the tube 4 is introduced into an electrical oven (not shown). The heating temperature of the oven is however below the fusion point of the electrolyte element, and of such a value that a logarithmic variation in the anhydride concentration will produce a proportional and substantially linear variation in the difference of potential detected at the electrodes 2 and 3, as graphically illustrated in FIG. 5.

Figure 2:
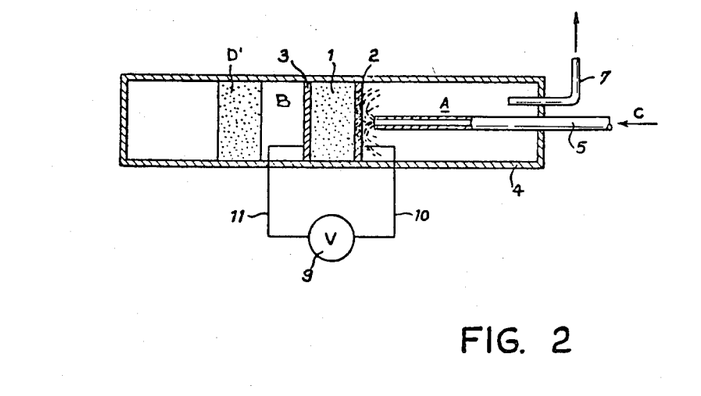
FIG. 2 shows a sensor in accordance with the present invention using the vapor pressure resulting of the thermo-decomposition of a metal salt of the anhydrides to be detected, in order to fix the thermodynamical partial pressure of a reference anhydride.

A modified arrangement of the embodiment shown in FIG. 1 is presented in FIG. 2 wherein a block D' of a metal salt of the anhydride to be detected is placed inside the then hermetically closed reference compartment "B". When heated, that metal salt D' evolves a metal oxyde and an anhydride identical to the one to be analyzed. For instance where $CO_2$ is the anhydride which is fed at "C", the corresponding metal salt chosen may then be $MCO_3$ which, when heated, will give $MO + CO_2$, the latter defining a partial pressure which will therefore produce a fixed reference potential at the reference electrode 3. Therefore, the thermodecomposition of a salt of the anhydride to be detected sets at the reference electrode a stable partial pressure which results in a fixed potential at that electrode, thereby allowing detection and measurement of the anhydrides to be analysed. The arrangement of FIG. 2 permits to avoid the reference gas circulating arrangement of FIG. 1. It is to be noted that by setting the metal salt block D' close to the reference electrode 3, the concentration of the reference anhydride evolved from D' remains stable, and then the compartment B does not need to be hermetically closed, but actually is open to air.

Figure 3:
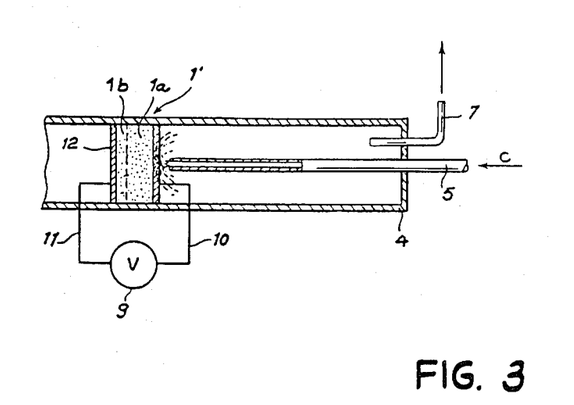
FIG. 3 shows another sensor in accordance with a further embodiment of the present invention using a solid electrode as a reference.

FIG. 3 illustrates a variant of the arrangement shown in FIG. 1. To the reference gas source "D" of FIG. 1 is substituted a solid state reference element. Then, the conduits 6 and 8 used for supplying and exhausting the reference gas from compartment "B" become superfluous and are eliminated. The use of a solid state reference is rendered possible owing to the use of a detecting element 1'. This element 1' is constituted through the sintering of a pure electrolyte compound 1a made of an alkali metal salt or an alkaline earth metal salt, which corresponds to the oxy-anions of the anhydride to be detected, and a second compound 1b made of the compound 1a to which a small amount of a metal salt has been added. The electrode 12 is then formed of a metal corresponding to the metal salt added by doping or vice-versa. For instance, if $K_2SO_4$ is used as compound 1a, the compound 1b will be constituted of $K_2SO_4$ doped with about 1% of $Ag_2SO_4$ or of AgCl, provided the electrode 12 is made of silver. The other numeral references indicated in FIG. 2 represent the same elements as those to which they refer in FIG. 1.

Although the arrangement of FIG. 3 is preferred, outstanding and useful results were obtained by solely using an electrolyte element made up of an homogeneous compound 1b only, that is without compound 1a. The reference electrode 12 is, in this case, always made of a metal identical to the metal of the doping metal salt, whereas the detection electrode is of any other metal.

Figure 4:
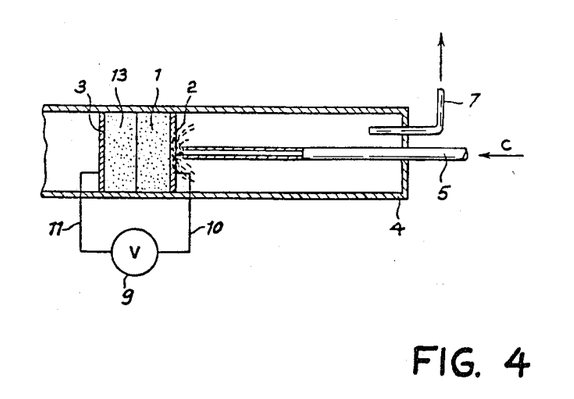
FIG. 4 shows another sensor in accordance with an embodiment of the present invention wherein the sensing element is formed of two juxtaposed compounds, one being an oxy-anion-bearing compound, at the anhydride measuring electrode, and the other containing an oxygen-bearing electrolyte at the reference electrode, the latter electrode generating a known potential when exposed to air or to oxygen having a given partial pressure.

FIG. 4 illustrates a further embodiment of a sensor having a solid state reference. In this embodiment, to the oxy-anion bearing compound 1 made of an alkali metal salt or alkaline earth metal salt is juxtaposed an oxygen-ion bearing electrolyte compound 13. A stable reference potential is thus produced at the reference electrode 3 whenever this electrode is exposed to ambient air or to oxygen, provided the oxygen partial pressure in air is constant, or when used in the arrangement of FIG. 6, described below.

As mentioned previously, the sensors shown in FIGS. 1 to 4 are introduced into an electric oven (not shown) so as to increase the sensing capacity of the electrolyte element. However, the temperature of the oven should not go beyond the melting point temperature of the electrolyte, and should be such that a logarithmic variation in the activity of the anhydride to be detected will result in a proportional and substantially linear variation of the potential detected. Therefore, the operating temperature having been selected, correct and useful measurement results are obtained, even if the activity or concentration of the anhydride varies from one measurement to another.

It is to be noted that the sensors illustrated in FIGS. 1 to 4 are able to produce potential differences in a range running from a few millivolts to several hundred of millivolts when a gaseous state compound is put into contact with the detecting part thereof.

Experiments were carried out by means of the arrangements illustrated in FIGS. 1 to 4 and certain results of which have been plotted on FIG. 5, which results will be discussed in connection with specific examples given hereafter.

Figure 6:
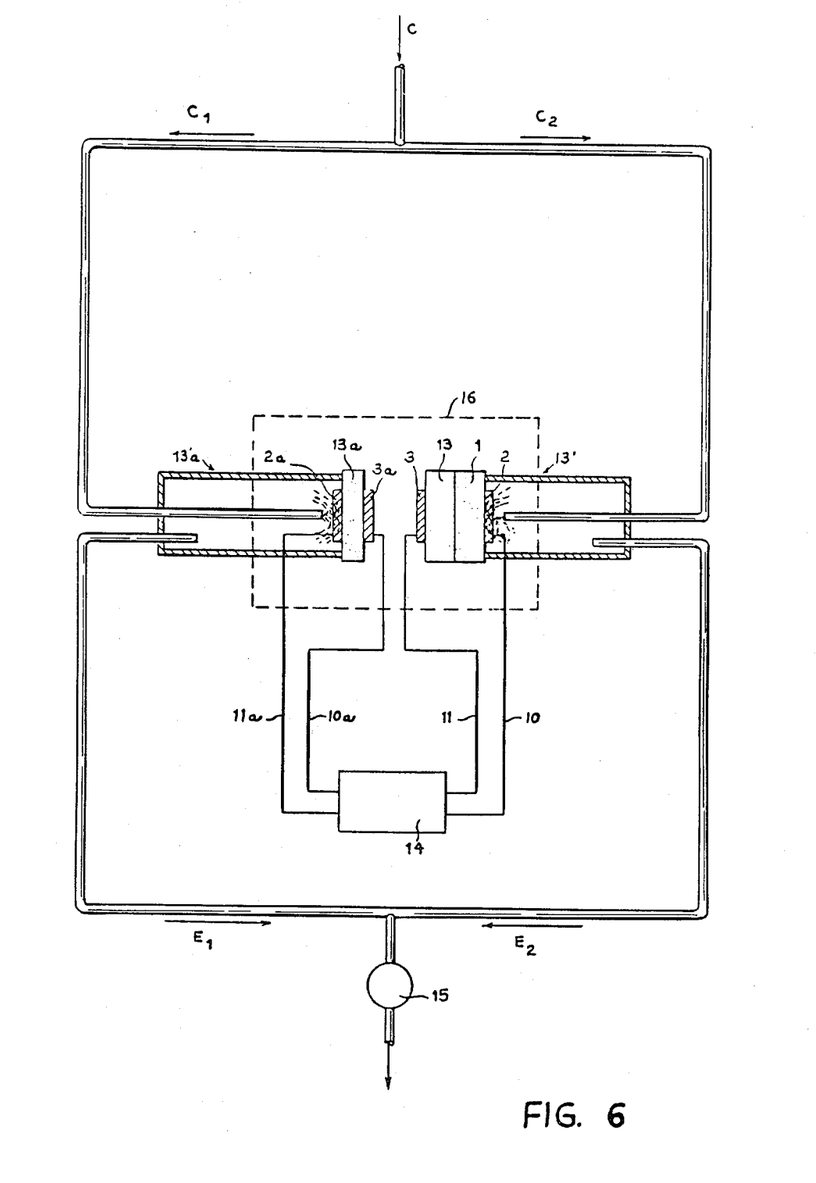
FIG. 6 shows an arrangement in accordance with an embodiment of the present invention to compensate for the oxygen partial pressure variations. The oxygen partial pressure in the gaseous sample is measured by means of a known oxygen sensor whereas the anhydride concentration is measured by anyone of the sensors described in FIGS. 1 to 4. The emf produced by both sensors are electronically corrected and substracted in order to produce an oxygen compensated signal of the anhydride concentration in the sampled gas.

FIG. 6 shows an arrangement to compensate for any variations in the partial pressure of the oxygen gas in the gaseous sample C. Actually, the anhydride detector is influenced both by a variation in the partial pressure of the anhydride and by a variation in the partial pressure of the oxygen in the sample. This phenomena does not interfere in environmental measurements since the oxygen partial pressure remains constant in air, but such variations are to be taken into account in stack gas analysis, for example, and other gases where the oxygen partial pressure fluctuates. To compensate for the oxygen partial pressure variations in a stack gas C, a portion C1 of this gas is fed to an oxygen sensitive detector $13'a$ made up of an oxygen-ion bearing electrolyte $13a$ having a reference electrode $3a$ and a measuring electrode $2a$, these two electrodes being of any electrically conductive material. Another portion C2 of the gaseous sample C is forwarded toward a second detector $13'$ which is identical to the one shown in FIG. 4. The reference electrodes 3 and $3a$ of detectors $13'$ and $13'a$, respectively, are exposed to ambient air. In addition, the two solid state detectors may be placed into the same electrical oven 16, as shown, or in two independent ovens in order to meet the operating temperature requirements of each detector. The potentials built-up at each electrode are sent to an analyser 14 which differentiates the signals from both detectors, thereby cancelling the variation effects of oxygen in the measurement of the anhydride concentration in the sample C. The sample gas is exhausted from both detectors through conduits $E_1$ and $E_2$, respectively, by means of a pump 15.

Although the arrangement illustrated in FIG. 6 has been described above with reference to detector $13'$, similar to the one shown in FIG. 4, it should be understood that anyone of the anhydride detectors of FIGS. 1 to 3 may as well be used. The use of the detector $13'$ in the arrangement of FIG. 6 being given by way of example only. On the other hand, the oxygen detector $13'a$ may be of any known type, and the one described in U.S. Pat. No. 3,400,054 issued on Sept. 3, 1968, to Ruka et al, may for instance, be advantageously utilized.

Figure 7:
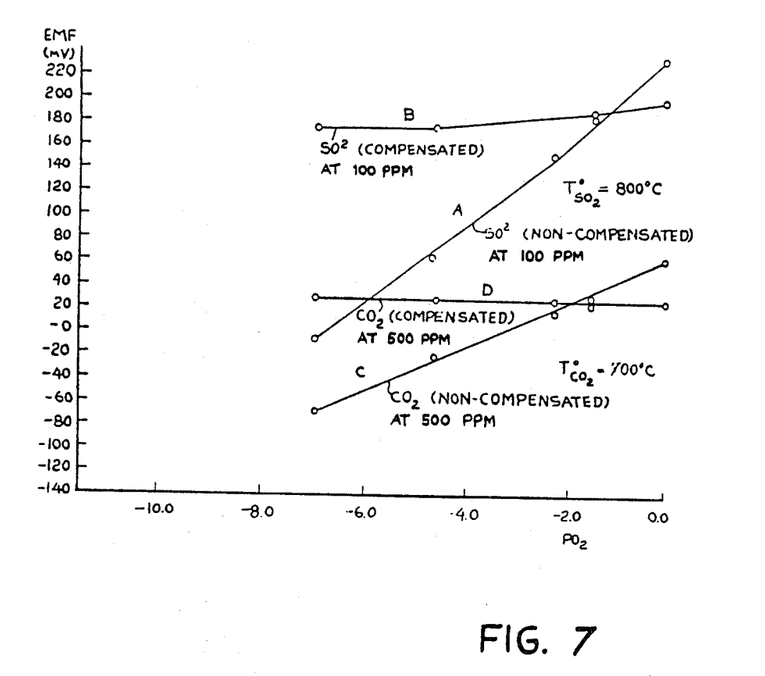
FIG. 7 shows graphs obtained from experiments carried out with the arrangement illustrated in FIG. 6.

Conclusive results have been obtained with the arrangement shown in FIG. 6, specific experimental results for $SO_2$ and $CO_2$ being presented on FIG. 7. An experiment carried on with $CO_2$ is further given below in example 7.

Figure 8:
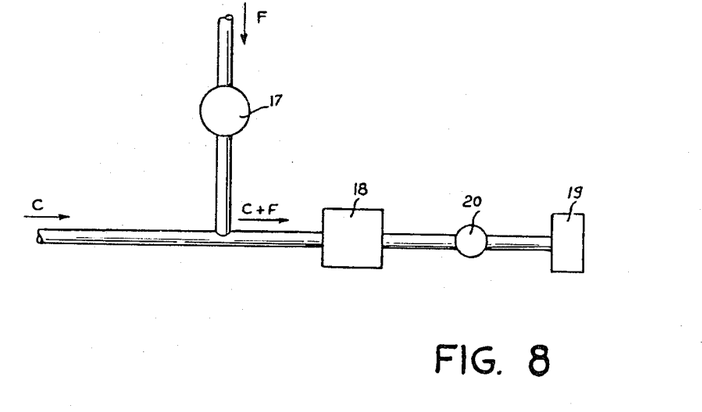
FIG. 8 shows another arrangement to compensate oxygen partial pressure variations in a gaseous sample. Compensation is achieved by injection of a fixed amount of oxygen rich gas into the stream of a sample gas entering the detector in order to increase its oxygen partial pressure to a nearly constant level.

FIG. 8 shows another arrangement suitable to compensate variations of the partial pressure of oxygen contained in a gaseous sample. Compensation is achieved by injecting a predetermined amount of an oxygen rich gas "F" into the incoming stream of a sample gas C, the flow of the oxygenated gas "F" being regulated by means of a flow-meter 17. Thus, the partial pressure of oxygen is increased to a level such that the potential difference measured by the voltmeter remains substantially unaffected by the oxygen concentration variations that may occur in the anhydride-containing sample gas, thereby enabling a true determination of the concentration of the anhydride to be detected by the detector 18, the latter being of the type described in anyone of FIGS. 1 to 4. It is therefore noted that the concentration of oxygen at the measuring electrode of detector 18 is substantially stable and proportional to the ratio F/C. A pump 19 controls the flow of the gas mixture, which flow value may be observed by means of the flow-meter 20.

Figure 9A:
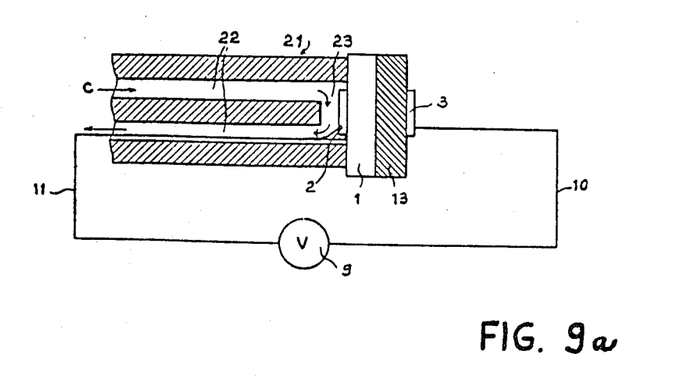
FIGS. 9a and 9b show a gas circulating system in which a measuring electrode wire runs through the outlet gas chambers.
Figure 9B:
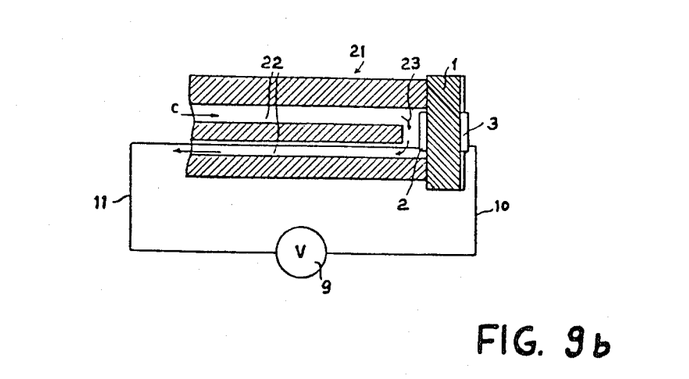
Figure 9C:
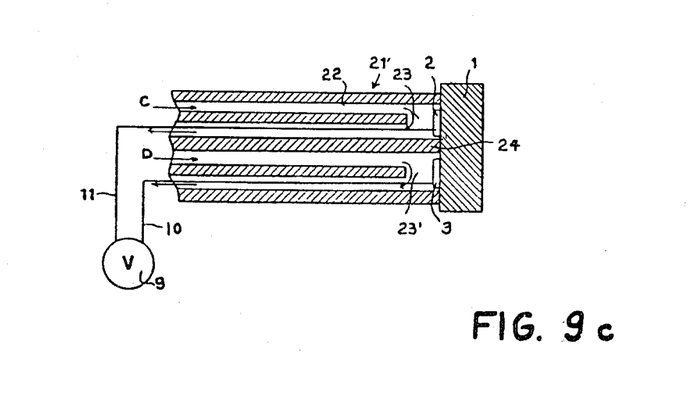
FIG. 9c shows a double independent gas circulating system, each of which being similar to the one shown in FIG. 9a. One of the gas conduits is used as the measuring system and the other as the gas reference system in which a known anhydride concentration is maintained.

Referring to FIGS. 9a, 9b and 9c, there are shown particular arrangements of the inlet and outlet conduits suitable to bring the anhydride to be detected and/or the reference gas in close contact with the corresponding electrode. Although these embodiments may appear quite simple, they have proven to be highly effective in hermetically sealing the contact points with the surface of the solid state sensors. As illustrated in FIGS. 9a and 9b, two substantially parallel channels 22 are pierced in a rod-like material 21, and thereafter the extreme portion 23 of the rod, that is the portion facing the measuring electrode 2, is cut off in order to provide a free gas flow path for sample C between the two channels. Sealing is effected by heating the electrolyte element to a temperature in the vicinity of its sintering temperature and then by pressing the extremity of the rod-shaped material provided with the opening 23 against the surface of the electrolyte element so as to slightly embedding the peripherical extremities thereof into the electrolyte element. A highly hermetical sealing is thus produced. Although in FIGS. 9a and 9b the particular conduit arrangement is used in connection with the sensors shown in FIGS. 4 and 3, respectively, it is understood that the above-described sealing method may be readily applied to any other types of solid state sensors, particularly those illustrated in FIGS. 1 and 2. In this respect, utilizing the solid state sensor of FIG. 1, an arrangement of a particular interest, being highly compact, is presented in FIG. 9c in which a plurality of substantially parallel channels 22′ have been pierced through the rod-like material 21′ and openings 23 provided at the rod extremity and in alignment with the respective measuring electrode 2 and reference electrode 3 to bring the sample gas C and the reference gas D in intimate contact with the corresponding electrodes. It is to be noted that with such arrangement both electrodes may be set at the same side of the solid state electrolyte element 1, thereby greatly increasing the compactness of the detector. A separatng wall 24 prevents the intermixing of the gas sample and the reference gas, this separating wall being also embedded into the element 1 in accordance with the sealing method mentioned above so as to sealingly separate the sample gas channel from the reference gas channel.

The rod-like material may be of ceramic, alumina, mullite, quartz or even of an abrasion resistent alloy.

The arrangement shown in FIG. 9 offers several advantages over hitherto known gas inlet and outlet conduits. Indeed, the present arrangement allows a direct contact of the gases with the different electrodes of the solid state electrolyte element and ensures the complete sealing of the various channels with respect to the environment and to other adjacent channels. Since the diameters of the channels are relatively small, their volume are reduced to a strict minimum and the gases, after having contacted the electrode, are promptly exhausted. Thus, the system response time, always influenced by gas dead volumes, is substantially increased and the true values of the potential corresponding to the anhydride concentration in the sample gas become available for analysis at the very start of the detecting proceedings. Moreover, it is to be noted that additional hermetically sealed channels may be provided for the leads connecting the various electrodes to the voltmeter 9, rather than running through the gas channels, as shown in FIG. 9c for instance.

Figure 10:
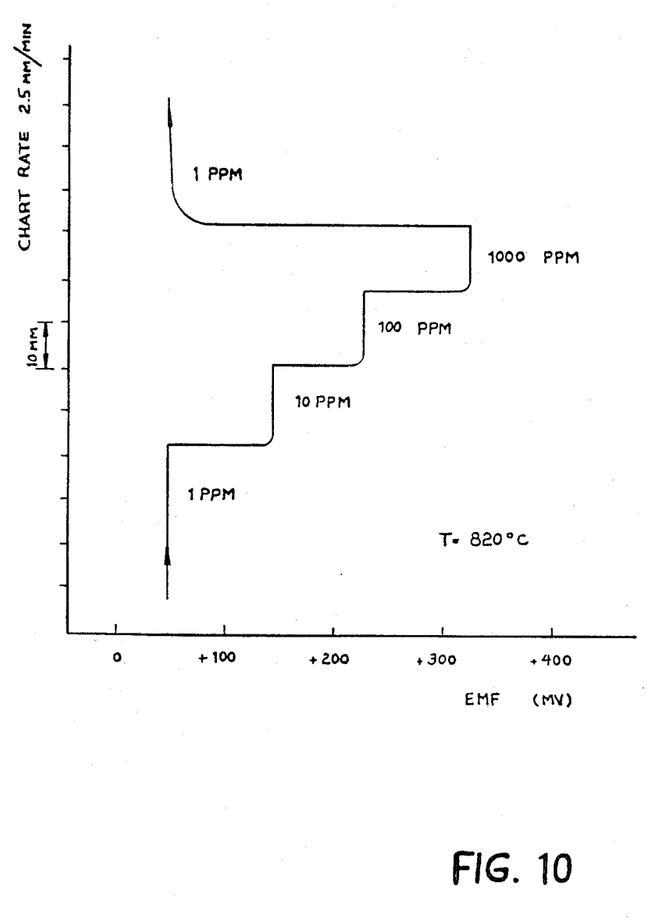
FIG. 10 shows the curve obtained from $SO_2$ concentration measurements effected by means of $K_2SO_4$/$ZrO_2$-CaO arranged as shown in FIG. 4 and using gas circulating system of FIG. 9a. This graphic representation shows the evolution of the emf signal at different $SO_2$ concentrations in function of the time.

We will hereinafter give some examples of experiments carried out by means of the arrangements illustrated in the abovedescribed figures with particular reference to the graphs shown in FIGS. 5, 7 and 10 on which experimental results have been quoted.

EXAMPLE 1

A series of tests were conducted using the arrangement of FIGS. 1 and 2 to monitor the amount of $SO_2$ in air. Various $SO_2$—Air mixtures were prepared and tested. In a concentration range running from 0.1 to 20,000 ppm, it was established that a linear relationship existed between the logarithm of the $SO_2$ content of the sampled gas and the electro-motive force recorded on the voltmeter.

EXAMPLE 2

A series of tests were conducted using the arrangement of FIG. 3 for samples such as $SO_2$, $H_2S$, $CH_3S$ and COS in air.

A pellet similar to that shown in FIG. 3 was used as a sensor. The pellet was of pure $K_2SO_4$ in contact with a porous platinum electrode and of $K_2SO_4$ doped with 1% of $Ag_2SO_4$ in contact with a porous silver electrode.

Each series of tests of a sulfur-bearing molecule in air at different concentrations gives a linear relationship between the log of the concentration of the sulfur-bearing compound and the difference of potential recorded on the voltmeter. The results obtained from samples of $SO_2$—Air, $H_2S$—Air and COS—Air are presented on FIG. 5.

It was also demonstrated that the presence of a high concentration of $NO_2$ in a tested sample does not affect the measurement of $SO_2$.

The detector of FIG. 3 was kept into operation for more than 5 weeks and proved to be stable and the results reproducible.

EXAMPLE 3

Another series of tests were effectuated by using the arrangement of FIG. 3 for determining the amount of $CO_2$, CO, COS, HCHO, $CH_3OH$, $(CH_3)_2CO$, $CH_4$, $C_2H_6$, $C_2H_4$ and $C_2H_2$ in air samples.

The sensing element used for those tests consisted of pure $K_2CO_3$ in contact with a porous platinum electrode and of $K_2CO_3$ doped with 1% of $Ag_2SO_4$ in contact with a porous silver electrode. The results obtained with different maxtures $CO_2$—Air are sumarized on FIG. 5 and demonstrate well the linearity of the measured values.

EXAMPLE 4

A series of tests were also performed with $N_2O$—Air, NO—Air and $NO_2$—Air mixtures using a nitrate pellet. Each pellet was of pure $Ba(NO_3)_2$ in contact with a platinum electrode and of $Ba(NO_3)_2$ doped with 1% of AgCl in contact with a silver electrode. The operating temperature of the system was in the range of 450° C.

The results obtained from different mixtures of nitrogen oxyde in the air indicate that the mixtures $NO_2$—Air gave rise to a linear emf signal with the pellet of nitrate. Those results with mixtures of nitrogen dioxyde—Air are reproduced on FIG. 5.

EXAMPLE 5

A series of tests were performed with the arrangement of FIG. 9a with various $SO_2$—Air samples.

A sensing element similar to the one shown on FIG. 4 was used as the sensor. The sensor was made of pure $K_2SO_4$ in contact with a $(ZrO_2)_{0.85}(CaO)_{0.15}$ electrolyte, both being in contact with porous platinum electrodes in air.

The series of tests obtained with the detector of FIG. 4, when using the oxygen of air as a reference, gave a linear relationship between the ln of the concentration of $SO_2$ and the electro-motive force recorded on the voltmeter.

The anhydride detector of FIG. 4 has proven to be highly stable and reproducible for a continuous operation of more than a month.

EXAMPLE 6

A series of tests were performed with the arrangement of FIG. 9c with various $AsH_3$—Air, $PH_3$—Air and $SeH_2$—Air samples. The sensing element used was similar to the one shown in FIG. 1.

It is to be noted that, in the vicinity of the detection electrode, each of those gases is readily converted into the corresponding anhydride, as shown by the following relations:

$$SeH_2 + 3/2O_2 \rightarrow SeO_2 + H_2O$$

$$2 AsH_3 + 3O_2 \rightarrow As_2O_3 + 3H_2O$$

$$2 PH_3 + 4O_2 \rightarrow P_2O_5 + 3H_2O$$

In the case of $AsH_3$, an electrolyte made of $Ca_3(AsO_4)_2$ was heated to a temperature of 800° C. and the reference gas contained 100 p.p.m. of arsine. The results are plotted in FIG. 5.

For $PH_3$ an electrolyte of $Ca_2P_2O_7$ was heated at 600° C. and 100 p.p.m. of phosphine was contained in the reference gas. The various resulting data are also computed in the graph of FIG. 5.

Concerning $SeH_2$, a $K_2SeO_4$ electrolyte was heated at 860° C. whereas only 5 p.p.m. thereof was contained in the reference gas. The potential differences for various concentrations of $SeH_2$ are indicated in FIG. 5.

Figure 5:
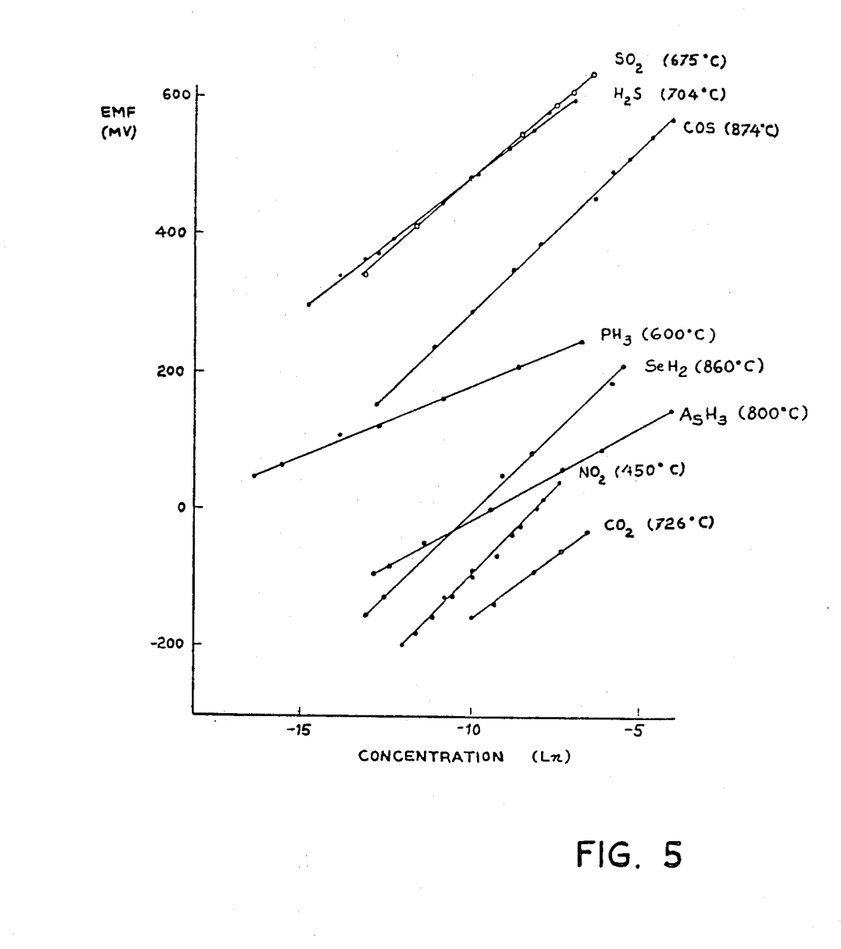
FIG. 5 shows a graph relating to the potential difference experimentally obtained for various concentrations of $SO_2$—Air, $NO_2$—Air, $CO_2$—Air, COS—Air, $PH_3$—Air, $AsH_3$—Air and $SeH_2$—Air mixtures. The sensors illustrated in FIGS. 1-4 were used to compile those results.

Consequently, the curves shown in FIG. 5 clearly illustrate the substantially linear relationship between the ln of the concentration of each gas to be detected and the potential differences measured by the voltmeter.

EXAMPLE 7

As mentioned above with reference to FIG. 6, the anhydride detector is influenced both by a variation in the partial pressure of the anhydride and of the oxygen in the sample. This phenomena does not however interfer in environmental measurements since the oxygen partial pressure is constant in air, but it has to be taken into account in stack gas analysis and other gases where the oxygen partial pressure may fluctuate.

With $CO_2$, for example, the above experimental observations may be translated by the following reaction:

$$CO_2 {\textstyle\frac{1}{2}} O_2 + 2e^- \rightleftharpoons CO_3^{2-}$$

which explains the form of the signal obtained at the electrode:

$$E_{signal} = E_o + (RT/4F) \ln pO_2 + (RT/2F) \ln pCO_2$$

E = the signal of the anhydride detector in volts
$E_o$ = a constant fixed by the composition of the reference electrode
R = gas constant
T = temperature in °K
F = Faraday number
$pO_2$ = oxygen partial pressure
$pCO_2$ = partial pressure of the carbon dioxyde in the sample On the other hand, it is known that the oxygen partial pressure can be measured with a zirconia stabilized oxygen detector which produces a following signal:

$$E_{pO_2} = E_o' + (RT/4F) \ln pO_2$$

where
$E_{pO_2}$ = Signal proportional to $pO_2$
$E_o'$ = a constant characterized by the material of the reference electrode.

The arrangement of FIG. 6 was used in order to verify the proposed mechanism of oxygen compensation for the $CO_2$ detector. The experimental results of FIG. 7, confirm such a mechanism and indicate that the electronic compensation of the signal from the $CO_2$ detector by the signal from the $O_2$ detector leads to a resulting signal which is independent of the concentration variations of the oxygen contained in the analysed gas sample.

With $CO_2$, compensation is obtained by directly opposing the signals from the two detectors. This same signal opposition principle may be applied in connection with any other anhydride detectors.

In certain cases, the oxygen detector signal has to be modified before being opposed to the signal from the anhydride detector. For example, in compensating for the signal from a $SO_2$ detector, it has been experimentally observed that the signal from this latter detector may be compensated by the signal from the oxygen detector if the oxygen signal is multiplied by two (2) before opposing it to the $SO_2$ signal. This fact can be mathematically demonstrated by introducing the equilibrium constant of the reaction ($SO_2 + {\textstyle\frac{1}{2}}O_2 \rightleftharpoons SO_3$) in the calculation of the signal from the $SO_2$ detector in the appropriate low concentration range of oxygen ($\leq 20\%$ $O_2$).

EXAMPLE 8

Another series of tests was made in order to demonstrate the performance and the reliability of the particular arrangement of FIG. 9a. The solid state detector used was a sensing element as shown on FIG. 4 and described in example 5. Sealing through thermal deformation was easily obtained at temperatures near the sintering temperature of the element. The curve shown in FIG. 10 clearly shows the short response time obtained with that arrangement since 90% of the signal is available in about 30 seconds from the start of the measurement. Such performances are mainly due to the short time spent by the gas at the measuring electrode, to the small dead volumes of the gas circuit and to the reduced adsorption surface.

EXAMPLE 9

Moreover, in order to demonstrate that the illustrated geometrical forms of the sensors are not limitative and that any form respecting the electrochemical principle of the sensor can be used and that multiple combination of the different preferred embodiments described above may be used to achieve a multi-function detector, tests were performed on a combination detector.

A combination detector made up of a sulfur anhydride detector, a carbon anhydride detector and an oxygen detector suitable to compensate for the oxygen variations in this sample gas (as mentioned in example 7 above) was built up. An oxygen ion electrolyte tube (one end closed), the electrolyte being for instance stabilized zirconia, was interiorly platinized in order to provide a common reference electrode with air ($pO_2 = 0.21$ atm). A first portion of the outside surface of the tube was covered with a $K_2SO_4$ electrolyte and another portion remote from the first portion with a $K_2CO_3$ electrolyte. These electrolyte layers were obtained by wetting the tube with the molten electrolyte or by a powder deposition technique, and were then sintered.

Then, two platinum wires were respectively turned around both electrolyte layers covering the tube outside surface to constitute the measuring electrodes for the two anhydrides to be detected whereas a third platinum wire was simply wound around the zirconia tube to constitute the measuring electrode used to compensate for oxygen partial pressure variations.

Therefore, when samples containing $SO_2$ and $CO_2$ were passed over this tube, emf signals identical to those shown in FIG. 7 have been obtained, which signals are proportional to the anhydride concentrations when the oxygen partial pressure varies.

We claim:

1. A method for measuring the activity of gaseous anhydrides in an oxygen-bearing gas comprising the steps of:

(a) providing a solid state electrolyte element having oxy-anions of the element forming the anhydride to be detected, said electrolyte element comprising one part made of an alkali metal salt or an alkaline earth metal salt supplying said oxy-anions and another part made of a mixture of said salt and of a metal salt; a detection electrode in contact with said alkali metal salt or said alkaline earth metal salt for creating a difference of potential when said anhydride to be detected comes into contact therewith and with said oxy-anion containing part of said electrolyte element; said detection and reference electrodes being arranged such that a potential difference occurs between said two elements when a sample of said anhydride to be detected is contacted with said detection electrode, said reference electrode being made of a metal identical to the metal of said metal salt and being in contact with said mixture; means for heating said electrolyte element to a temperature such that a logarithmic variation in concentration of the anhydride to be detected causes a proportional and substantially linear variation in said difference of potential, said temperature being below the fusion temperature of said electrolyte element, and a potentiometric measurement means connected to said electrodes for measuring the activity of said anhydride to be detected by measuring said difference of potential;

(b) passing said oxygen-bearing gas containing said anhydride material into contact with said detection electrode and said electrolyte so as to create a potential difference between said two electrodes; and (c) measuring said potential difference with said potentiometric measurement means to determine the anhydride content of said gas.

2. A method of detecting the activity of gaseous anhydrides in oxygen-bearing gas comprising the steps of:

(a) providing a first sensing arrangement including a solid state electrolyte element having oxyanions of the element forming the anhydride to be ditected, a reference electrode in contact with the electrolyte element, a detection electrode remote from said reference electrode and also in contact with said electrolyte element, said detection and reference electrodes being arranged such that a difference of potential occurs when the anhydride to be detected is contacted with said detection electrode and with the electrolyte element, means for heating the electrolyte element to a temperature such that a logarithmic variation in the activity of the anhydride to be detected causes a proportional and substantially linear variation in said difference of potential, said temperature being below the fusion temperature of the electrolyte element; a second sensing arrangement for detecting variations in the activity of the oxygen-bearing gas, including an oxygen ion-bearing electrolyte for sensing the oxygen content variations in said oxygen-bearing gas, a reference electrode and a measuring electrode both in contact with said oxygen ion-bearing electrolyte heated to the operating temperature of said first sensing arrangement for producing a second difference of potential representative of oxygen gas concentration variations in said sample gas, and means connected to said electrodes of said first and second arrangements for measuring the activity of said anhydride by measuring the difference between said first and second differences of potential;

(b) passing said anhydride containing oxygen-bearing gas into contact with said detection electrode of said first sensing arrangement to create a first difference of potential and passing said oxygen-bearing gas into contact with said measuring electrode of said second sensing arrangement to cause a second difference of potential; and (c) measuring the activity of said anhydride by measuring the difference between said first and second differences of potential with a potentiometric measurement means.

* * * * *